United States Patent [19]

Catalucci

[11] 4,071,550

[45] Jan. 31, 1978

[54] PROCESS FOR THE PRODUCTION OF AMINOCYANOACETIC ACID ETHYL ESTER

[75] Inventor: Enrico Catalucci, Visp, VS, CH Switzerland

[73] Assignee: Lonza, Ltd., Gampel, Valais, Switzerland

[21] Appl. No.: 759,027

[22] Filed: Jan. 13, 1977

[30] Foreign Application Priority Data

Jan. 13, 1976 Switzerland .............................. 312/76

[51] Int. Cl.$^2$ ........................................... C07C 120/00
[52] U.S. Cl. ................................................ 260/465.4
[58] Field of Search ......................... 260/465.4, 583 M

[56] References Cited

PUBLICATIONS

Cook, et al., C.A. 44, (1950), 1965e.
Ohta, C.A., 48, (1954), 4404 G–h.
Cook, C.A., 49, (1955), 3166a.

*Primary Examiner*—Joseph P. Brust
*Attorney, Agent, or Firm*—Virgil H. Marsh

[57] ABSTRACT

In the process for the production of the ethyl ester of aminocyanoacetic acid by reduction of the ethyl ester of nitrosocyanoacetic acid, the improvement of hydrogenating the ethyl ester of nitrosocyanoacetic acid in a low-boiling polar solvent in the presence of Raney nickel at an excess pressure with hydrogen of 1 to 10 atms. and at a temperature of 10° C. for 40 hours to 60° C. for 8 hours.

3 Claims, No Drawings

PROCESS FOR THE PRODUCTION OF AMINOCYANOACETIC ACID ETHYL ESTER

BACKGROUND OF THIS INVENTION

1. Field of This Invention

This invention relates to a process for the production of the ethyl ester of aminocyanoacetic acid.

2. Prior Art

Nitrosocyanocetic acid ethylester has been reduced in moist diethylether with amalagamated aluminum (Chemical Abstracts, 48, (1954), 4440 g.). Such a process is difficult to carry out, since amalgamated aluminum is cumbersome to produce and the diethylester must be used as a solvent in large quantities because of strong dilution, which is accompanied by considerable danger.

BROAD DESCRIPTION OF THIS INVENTION

It is an object of this invention to provide a process which permits the production of the ethyl ester of aminocyanoacetic acid in a simple manner and with a good yield. Other objects and advantages of this invention are set out herein or are obvious to one ordinarily skilled in the art herefrom.

The objects and advantages of this invention are achieved by the process of this invention.

The process of this invention involves hydrogenating the ethyl ester of nitrosocyanoacetic acid in a low-boiling polar solvent in the presence of Raney nickel at an excess pressure with hydrogen of 1 to 10 atms. and at a temperature of 10° C. for 40 hours up to 60° C. for 8 hours. In the preferred embodiment, an alcohol with 1 to 3 carbon atoms, preferably, methanol, ethanol or a propanol, is used as the polar, low-boiling solvent. The preferred range of the excess pressure with hydrogen during hydrogenation is 3 to 5 atms.

The process of this invention involves the low pressure hydrogenation of the ethyl ester of nitrosocyanoacetic acid in the presence of a (known) commercial Raney nickel hydrogenation catalyst. In order to limit any under or over hydrogenation to a minimum, the hydrogenation temperature must be kept within a certain range, i.e., that is stated herein. Preferably the ethyl ester of nitrosocyanoacetic acid is hydrogenated at a temperature of 35° to 45° C. during 10 to 13 hours.

The aminocyanoacetic ester formed can be isolated in the form of its toluene sulfonate, which can be stored and can be used as such, owing to its solubility in most organic solvents, in different reactions. The product obtained by applicants consists of beige to light brown crystals having a melting point of 114° to 115° C. It can absorb, upon standing, 5 to 11 percent (corresponding to 1 to 2 moles of water of crystallization per mole of tosylate) and can be stored as a hydrate at ambient temperature.

The ethyl ester of aminocyanoacetic acid is a versatile reagent which may be used in various syntheses, for example, those of inidazoles, thiazoles and pyrazines. [See: Cook, A.H., Chem. Soc., (1949), p. 1072; *Cook, A.H.*, J. Chem. Soc., (1947), p. 1596; *Cook, A.H.*, J. Chem. Soc. (1949), p. 1446, 1607; *Robinson, D.H.*, C.A., 77, 101464 (1972); and *Taylor, E.C.*, J. Am. Chem. Soc., 95, 6047, (1973).]

DETAILED DESCRIPTION OF THIS INVENTION

As used herein, all parts, ratios and percentages are on a weight basis, unless otherwise stated or otherwise obvious to one ordinarily skilled in the art.

EXAMPLE 1

20.0 gm. of technical nitrosocyanoacetic acid ethyl ester (melting point 130° to 133° C.), 200 ml of absolute ethanol and 3 gm. of moist, commercial Raney nickel (corresponding to 2 gm. of dry Raney nickel) were placed into a 1-liter steel autoclave, which had a paddle stirrer, and were hydrogenated at 1000 UpM., at a $H_2$ pressure of 4 kg/cm$^2$ and at 40° C. for 11 hours. After hydrogenation was completed, the catalyst was removed by filtration and the filtrate was mixed with 26.7 gm. of toluene sulfonic acid hydrate. Then the ethanol was distilled off using a rotary evaporator. The residue was suspended in a total of 500 ml of ether (in portions of 165 ml), was stirred and filtered off. After drying the filter residue (filtrate) at 35° C., 28.7 gm. (65 percent of theory, based on the amount of nitrosocyanoacetic acid ethyl ester) of the ethyl ester of aminocyanoacetic acid-tosylate was isolated as a beige powder. Upon standing the product absorbed water vapor to a 11 percent level.

EXAMPLE 2

Hydrogenation was carried out under the same conditions as in Example 1 at 30° C., using the same apparatus and ingredients of Example 1. After 8 hours a sample of 20 ml was taken and filtered; and the filtrate was evaporated until dry. The residue (1.43 gm.; 80 percent of theory, based on the amount of nitrosocyanoacetic acid ethyl ester) was analyzed. The IR-spectrum showed insufficient hydrogentation. Hydrogenation was then continued at 40° C. for 4 hours. A sample of 20 ml was removed and treated as above. 1.40 gm. of aminocyanoacetic acid ethyl ester was obtained (78 percent of theory). The IR spectrum of the product was identical to that of pure aminocyanoacetic acid ethyl ester obtained by AC-HG reduction.

EXAMPLE 3

The experiment shown in Example 1 was repeated, whereby the starting material was hydrogenated for 16 hours at 40° C. The IR spectrum of a sample, isolated as in Example 2, showed overhydrogentation. The residual reaction mixture was processed as in Example 1. Aminocyanoacetic acid ethyl ester-tosylate was isolated in the form of brown crystals in a yield of 51 percent, based on the nitrosocyanoacetic acid ester ester.

EXAMPLE 4

99.5 gm. of technical nitrosocyanoacetic acid ethyl ester (melting point: 130° C.), 1 liter of absolute alcohol and 15 gm. of moist Raney nickel are placed into a 2-liter steel autoclave, which had a paddle stirrer. The mixture was hydrogenated for 10.5 hours at 1000 UpM., at a $H_2$ pressure of 4 kg/cm$^2$ and at 40° C. After hydrogentation was completed, the catalyst was removed by filtration. The filtrate was mixed with 133.3 gm. of p-toluene sulfonic acid hydrate. The mixture was evaporated on a rotary evaporator. The residue was washed using portions (with a total of 3.5 liters) of ether as in Example 1. After drying, 149.2 gm. of aminocyano acetic acid ethyl ester tosylate was obtained as a beige powder (70 percent of theory, based on the amount of nitrocyanoacetic acid ethyl ester was used). The product upon standing absorbed water vapor to a level of 5.6 percent.

What is claimed is:

1. In the process for the production of the ethyl ester of aminocyanoacetic acid by reduction of the ethyl ester of nitrosocyanoacetic acid, the improvement characterized in that said ethyl ester of nitrosocyanoacetic acid is hydrogenated in a solvent which is selected from the group consisting of methanol, ethanol and a propanol in the presence of Raney nickel at an excess pressure with hydrogen of 1 to 10 atms. and at a temperature of 10° C. for 40 hours to 60° C. for 8 hours.

2. A process as claimed in claim 1 wherein said hydrogenation is carried out at an excess pressure with hydrogen of 3 to 5 atms.

3. A process as claimed in claim 1 wherein said ethyl ester of nitrosocyanoacetic acid is hydrogenated at a temperature of 35° to 45° C for 10 to 13 hours.

* * * * *